(12) United States Patent
Pacca

(10) Patent No.: US 11,986,393 B2
(45) Date of Patent: May 21, 2024

(54) DEVICE AND METHOD FOR GENERATING AN ELECTRIC CURRENT IN A CONDUCTOR FOR REMOVAL OF BIOFILM

(71) Applicant: Daniel Moreira Pacca, Sao Paulo (BR)

(72) Inventor: Daniel Moreira Pacca, Sao Paulo (BR)

(*) Notice: Subject to any disclaimer, the term of this patent is extended or adjusted under 35 U.S.C. 154(b) by 677 days.

(21) Appl. No.: 16/748,330

(22) Filed: Jan. 21, 2020

(65) Prior Publication Data
US 2021/0106429 A1  Apr. 15, 2021

(30) Foreign Application Priority Data
Oct. 14, 2019 (BR) .......................... 102019021568-2

(51) Int. Cl.
*A61F 2/38* (2006.01)
*A61F 2/30* (2006.01)
*A61F 5/01* (2006.01)
*A61L 2/03* (2006.01)
*A61N 2/00* (2006.01)
*A61N 2/02* (2006.01)

(52) U.S. Cl.
CPC .................. *A61F 2/38* (2013.01); *A61L 2/03* (2013.01); *A61N 2/004* (2013.01); *A61N 2/02* (2013.01); *A61F 2002/30668* (2013.01); *A61F 2310/00017* (2013.01); *A61F 2310/00023* (2013.01); *A61F 2310/00029* (2013.01)

(58) Field of Classification Search
CPC . A61F 2/38; A61F 2002/30668; A61N 2/004; A61N 2/02
See application file for complete search history.

(56) References Cited

U.S. PATENT DOCUMENTS

| | | | |
|---|---|---|---|
| 2011/0230701 A1* | 9/2011 | Simon | A61N 1/0456 607/46 |
| 2012/0330090 A1* | 12/2012 | Sham | A61N 2/002 600/13 |
| 2015/0076000 A1 | 3/2015 | Ehrensberger et al. | |
| 2017/0056536 A1 | 3/2017 | Hallab et al. | |

* cited by examiner

*Primary Examiner* — Thaddeus B Cox
*Assistant Examiner* — Joshua Daryl D Lannu
(74) *Attorney, Agent, or Firm* — Lippes Mathias LLP

(57) ABSTRACT

The present invention is a device and a method to generate an electric current in a conductor (15). More specifically, the present invention is a device (10) that comprises a magnetic field generator element (11), a control element (12), and a support element (14). The magnetic field generator element (11) and the control element are electrically assembled, the magnetic field generator element (11) is designed to generate a varying magnetic field (B). The aforementioned varying magnetic field (B) comprises at least one varying parameter, the control element (12) is designed to control at least one varying parameter, and the support element (14) is designed to hold the magnetic field generator element (11), and the control element.

5 Claims, 5 Drawing Sheets

DEVICE AND METHOD FOR GENERATING AN ELECTRIC CURRENT IN A CONDUCTOR FOR REMOVAL OF BIOFILM

CROSS-REFERENCE TO RELATED APPLICATION

This application claims priority under 35 USC 119 to Brazilian Patent Application No. BR102019021568-2 filed Oct. 14, 2019, and the entire disclosure of said Brazilian application is hereby incorporated by reference in its entirety into the present specification.

FIELD OF INVENTION

This invention is a device designed to generate an electric current in a conductor and a method for generating an electric current in an electric conductor with this device.

BACKGROUND OF THE INVENTION

The world population is growing every day and there is progress in access to health. We are facing a demographic transition with an increasingly high proportion of elderly people.

Therefore, the number of people with medical implants tends to increase, as well as the complications of these implants, the infections for example. An estimated 1 million cases of infection occur each year in the United States, with a treatment cost of 50 thousand dollars per patient.

Besides the costs involved, another known complication of the state of art is the development of the biofilm on these implants. The biofilm arises on several materials, for example, plastic, metallic, Teflon, etc. In metallic implants, the biofilm formation precludes the appropriated penetration of the antibiotics. Therefore, the treatment is based on surgical procedures with the need for hospital admission, procedures with an open approach, prolonged therapy with antibiotics, exchange or withdrawal of the prosthesis, prolonged rehabilitation periods, those having great impact on morbidity, mortality and economic/social aspects.

The abovementioned biofilm is a structured community of bacteria embedded in a polymeric matrix produced by themselves. These polymeric substances offer protection for the bacteria against several types of attacks to which they are exposed, for example, the use of an antibiotic or a chemical substance to remove them.

An attempt to solve these problems lies in using electricity to reduce the bacteria colony in the biofilm of the implants.

The Patent Application published in the United States No. US2015/0076000, reveals a method to reduce or prevent the growth of microorganisms on the surface of a medical implant using a counter-electrode and a reference electrode. The implant is taken as the working electrode. The electric current flows through the working electrode and the counter-electrode. The electric current through the counter-electrode varies, so the electric potential of the working electrode remains constant in relation to the electric potential of the reference electrode.

However, the method disclosed in said document does not solve one of the most important drawbacks of these medical procedures, which is the compulsory requirement of invasive procedures. In other words, to use that method it is necessary to make an opening in the part of the body where the electrode is located, in order to enable the association of the reference electrode and the counter-electrode to the implant and enable the creation of an electric circuit.

Similarly, the Patent Application published in the United States No. US2017/0056536 reveals a method extremely similar to the method disclosed in document US 2015/0076000, in which a reference electrode, a counter-electrode, and a potentiostat are connected to a prosthesis. According to the description of an embodiment of the invention, the prosthesis has a conductive surface area and a segment that is partially placed in the bone of a residual member. In this scenario, the potentiostat is connected to the conductive surface of the prosthesis, and the other two electrodes are connected to the potentiostat and to the external surface of the residual member. Therefore, the potentiostat and the two electrodes make up a three-point electrochemical cell.

However, this method also requires a surgical procedure to make possible the connection between the electrodes and the potentiostat directly with the prosthesis.

Thus, no device and/or method is observed in the state of the art that allows the prevention and/or removal of a biofilm formed on the surface of metal implants.

The present invention solves these problems by providing a device and a method that makes it possible to prevent the biofilm formation on the surface of metal implants and/or the complete removal of a biofilm layer already built. Furthermore, it uses a device that reaches such solutions in a noninvasive manner, and thus not require any surgical intervention.

SUMMARY OF THE INVENTION

A first objective of the invention lies in providing a device that is capable to generate an electric current in a conductor.

A second objective of the invention lies in providing a device that is capable to generate an electric current in a conductor that has portable dimensions.

A third objective of the invention lies in providing a method of generating an electric current in a conductor.

These and other objectives of this invention are achieved through a device that is able to generate an electric current in a conductor. The device comprises a magnetic field generator element, a control element, a support element, and an energy source. The magnetic field generator element, the control element, and the energy source are electrically assembled to each other. The magnetic field generator element is designed to generate a varying magnetic field, this varying magnetic field comprising at least one varying parameter. The control element is designed to control at least one varying parameter, and the support element is designed to hold the energy source, the magnetic field generator element, and the control element.

Furthermore, the objectives of this invention are met through a method of generating an electric current in a conductor with a device able to generate an electric current in the conductor, wherein the device comprises a magnetic field generator field, a control element, a support element, and an energy source, the magnetic field generator element and the control element are electrically assembled, the magnetic field generator element is designed to generate a varying magnetic field, the varying magnetic field comprises at least one varying parameter, the control element is designed to control at least one varying parameter, and the support element is built to hold an energy source, the magnetic field generator element, and the control element, wherein the method comprises the following steps:

(a) to establish at least one value of the desired electric current;
(b) to establish a period of time for the device to operate;
(c) to set at least one varying parameter;
(d) to generate a varying magnetic field;
(e) to approach the device and the conductor; and
(f) to induce the electric current in the conductor.

Additionally, the objectives of this invention are met through a method of removing biofilm from an internal conductor in a patient using a device able to generate an electric current with at least one varying parameter in the conductor, wherein the device comprises a magnetic field generator field, a control element, a support element, and an energy source, the magnetic field generator element and the control element are electrically assembled, the magnetic field generator element is designed to generate a varying magnetic field, the varying magnetic field comprises at least one variable parameter, the control element is designed to control at least one varying parameter, and the support element is built to hold an energy source, the magnetic field generator element, and the control element, wherein the method comprises the following steps:
  (i) to establish at least one varying parameter of the electric current required to treat the biofilm on the conductor,
  (ii) to establish the period of time in which the electric current must be applied to the conductor,
  (iii) to position the support element on the patient's body where the conductor is placed,
  (iv) to activate the device, and
  (v) to generate an electric current with the electric current intensity established in step (i), during the period of time established in step (ii).

Furthermore, the objectives of this invention are achieved also by means of a method of treatment of a person that needs the removal of the biofilm on a metallic prosthesis implanted in his body, wherein the method comprises the following steps:
  (a) to establish the value of at least one parameter of the desired electric current;
  (b) to establish the period of time to the device to operate;
  (c) to set at least one varying parameter of the varying magnetic field;
  (d) to generate a varying magnetic field;
  (e) to approach the device to the metallic implant; and
  (f) to induce an electric current on the metallic implant.

BRIEF DESCRIPTION OF THE DRAWINGS

The present invention will now be described in greater detail based on a sample execution represented in the drawings. The drawings show.

DETAILED DESCRIPTION OF THE INVENTION

As widely known in the state of art, the microorganisms that grow on the surface of the implants made of several materials, after being introduced in the human body, may build what is named the biofilm.

As mentioned earlier, biofilms are structured co-units of bacteria that are soaked in polymeric matrices produced by themselves. Such polymeric substances provide the bacteria protection against several types of aggression that they may suffer such as, for example, the use of antibiotic drugs or chemical agents for their removal.

In this scenery, it is common to observe the formation of a biofilm on medical implants where an infection has occurred. The infection of medical implants, more specifically the infection of prostheses, occurs in approximately 2.4% of patients with knee prostheses and in up to 40% of patients with cardiac prostheses. The required treatment is most commonly a surgical and invasive approach, in which several procedures can be performed, such as hospital admissions, rehabilitation periods and intensive treatment, or even the removal and/or exchange of the prosthesis.

Such procedures may lend to other future complications. This is because, when any surgical procedure is performed, there is a risk of other infections, as well as possible clinical complications resulting from such surgical procedures.

As stated earlier, this situation occurs due to the fact that the biofilm build on the surface of medical implants precludes the immediate therapeutic effect of antibiotic therapy as such biofilm protects bacteria from the effects of these products. As a result, the antibiotic-only treatment is usually an ineffective method in such situations, and it should, therefore, be performed with surgical intervention.

However, one way to maximize antibiotic action is to use electricity to weaken the membranes of organisms in the biofilm. Usually, invasive devices are used, positioned through an incision made at the implant site. The device is then connected to the implant and an electrical current is generated for a certain period of time. It is noteworthy that the above process has not been used in the clinical practice, and even in the experimental context, only invasive processes are known.

Anyway, and as already mentioned above, the need for performing an incision in the place of the implant is an undesirable feature that is solved with the present invention.

That is because the present invention provides a device 10 and a method of generating an electric current in a conductor 15 in a non-invasive manner, so it prevents and/or treats the formation of biofilm on a conductor 15, as we will state in the following text.

Figure 1:
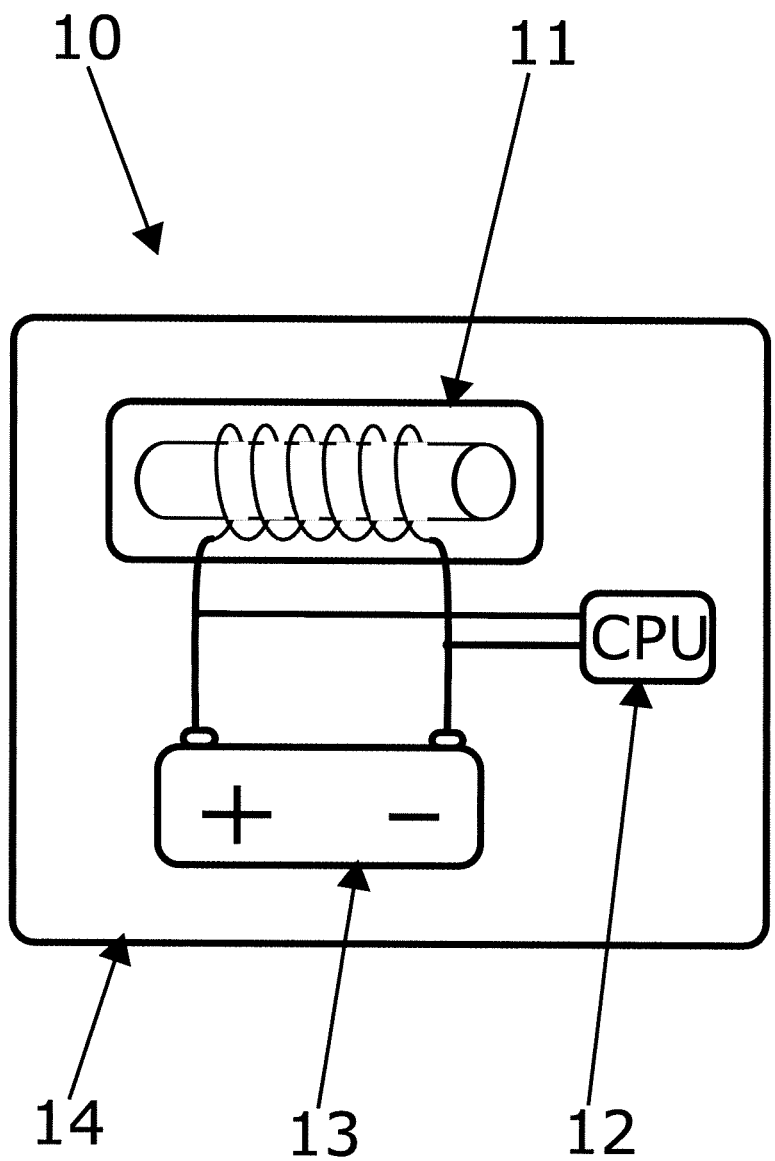
FIG. 1—shows the device proposed herein and its elements.
Figure 2:
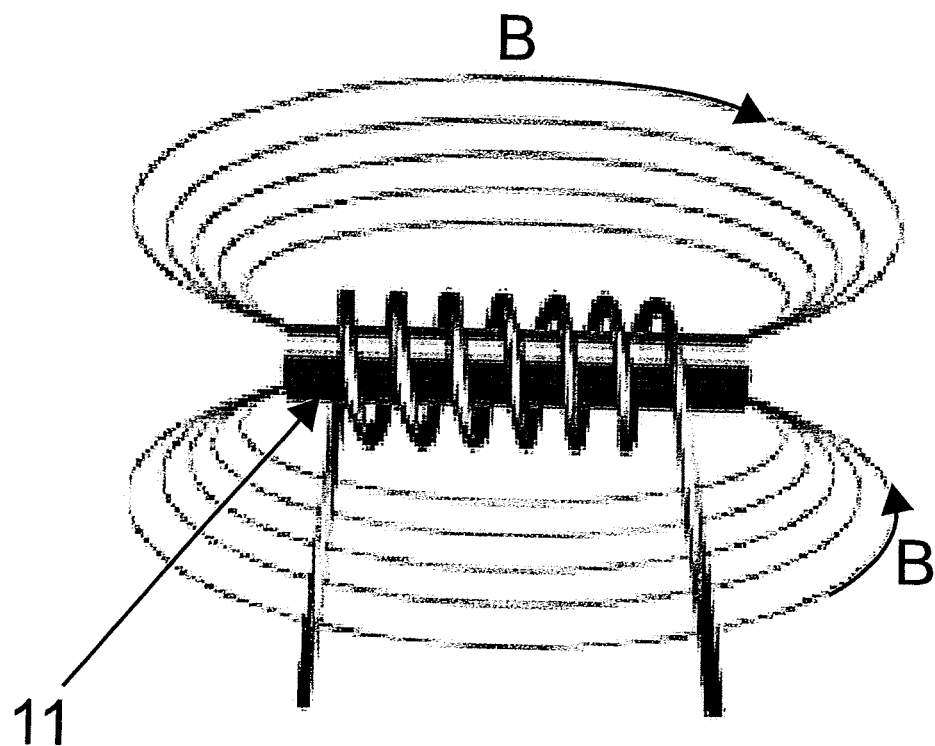
FIG. 2—shows the magnetic field generator element, comprised in the proposed device.
Figure 3:
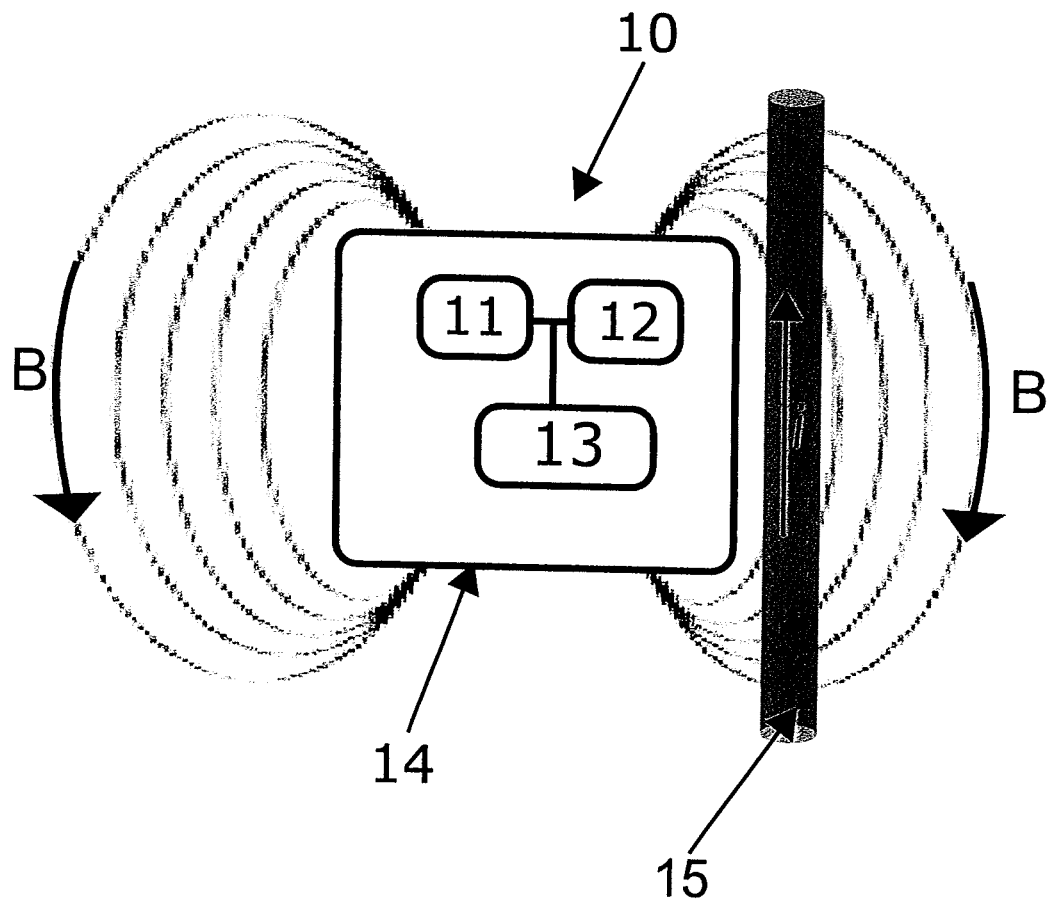
FIG. 3—shows an embodiment of the present invention, in which the device induces a current in a conductor through the generation of an electromagnetic field.

As can be seen in FIGS. 1 and 3, a device 10 capable of generating an electric current in a conductor 15 is illustrated. Such a device comprises a magnetic field generator element 11 electrically assembled to a control element 12, both of them electrically assembled to an energy source 13 and mechanically assembled to a support element 14.

The magnetic field generator element 11 is designed to generate a varying magnetic field B with at least one varying parameter. This parameter may be any physical variable of the generated magnetic field including, but not limited to, the intensity of the magnetic field, the polarity of the magnetic field, a position in the magnetic field, etc.

That varying parameter is controlled by the control element 12. This control element may be, ideally, a microprocessor with a software, as well as any other electronic control device already known in the state of art.

Additionally, the magnetic field generator element 11 and the control element 12 are electrically powered by the source of energy 13. For example, the energy source could be a battery. However, such an example should not be understood as a limitation of the present invention since the source of energy 13 can be any device capable of electrically feeding the device 10, i.e., providing energy for the operation of the magnetic field generator element 11 and the control element 12.

Moreover, in only one of the possible executions that will be described below, the energy source 13 must be always deemed as being electrically associated with the magnetic field generator element 11 and to the control element 12. Therefore, throughout this document, when the magnetic field generator element 11 and the control element 12 are referred to, it must be understood that the energy source 13 is also present.

Figure 4:
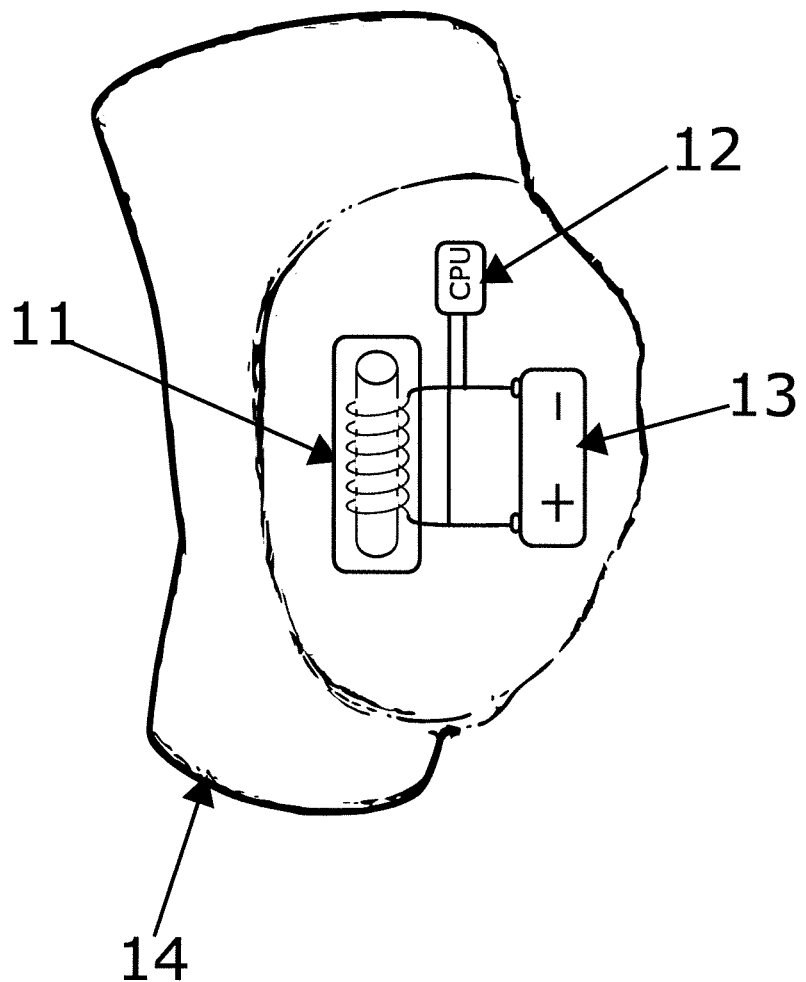
FIG. 4—shows the proposed device, held in the support element.
Figure 5:
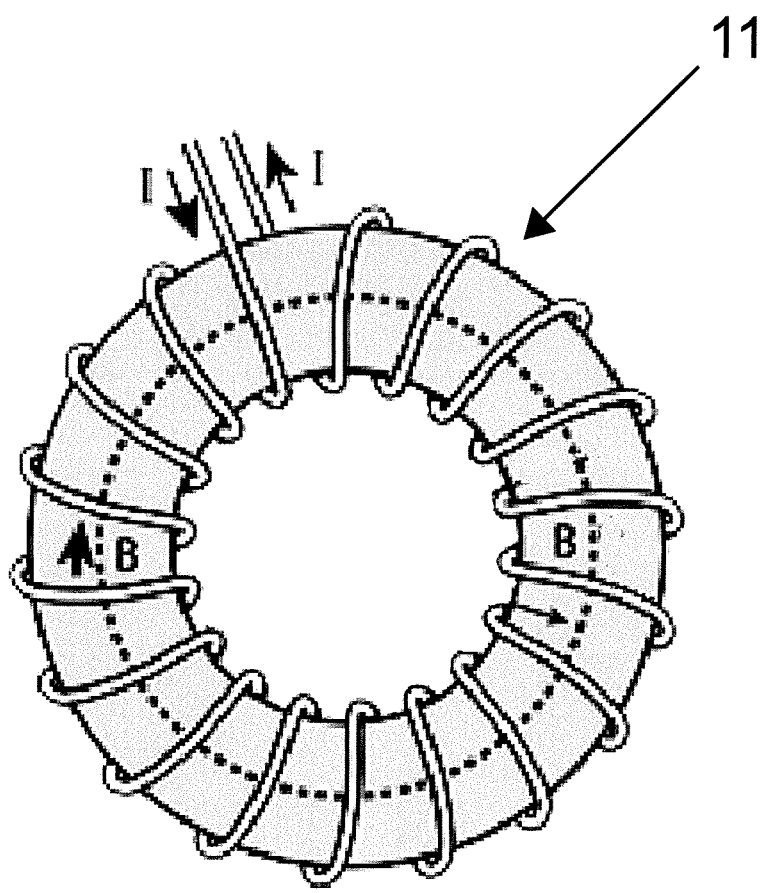
FIG. 5—shows one possible embodiment of the magnetic field generator element, represented as a toroidal coil.

The FIGS. 4 and 5 show one of the possible executions of this invention in which the magnetic field generator element 11 is a toroidal coil and the energy source 13 is a battery. The toroidal coil and the battery are designed to be held in the support element 14 that, in an illustrative manner only and in this preferential execution, is an elbow or knee brace.

However, the execution above is not to be understood as a limitation to the present invention. The magnetic field generator element 11 may be any device or apparatus known to be able to generate a varying magnetic field, such as an electromagnet. Similarly, the support element 14 may be any other element that is capable to hold the magnetic field generator element 11, either inside or outside of it.

In any case, the preferential embodiment described above has the objective of providing a device 10 capable to generate an electric current in a conductor 15, in a way that this device 10 is a portable one, i.e., it is sized to be held in an elbow or knee brace.

Furthermore, the conductor 15, in which an electric current will be generated to operate the device is, in an only preferential way, a metallic implant. More preferably, the metallic implant is a metallic prosthesis internally arranged to the human body in the knee region. More preferably still, the metallic implant is a metallic knee prosthesis made of chromium cobalt.

However, such characteristics should not be understood as a limitation of this invention, being only an example of one of the possible executions. The conductor 15 can be any metallic conductor fit to have an electric current induced in itself. In addition, the conductor 15 can be a metallic implant positioned in any region of the human body, and can also be made of any metal alloy used in the state of the art, such as titanium, steel, Teflon, etc.

In harmony with the information presented so far, the device 10 will, when in operation, induce an electric current in the desired conductor 15.

This result occurs due to the physical effects resulting from several known laws of the state of the art. By way of example only and in a non-limiting way, the Faraday Law and the Biot-Savart Law are related to the appearance of a potential difference and a current flow in an electrical conductor in the presence of a magnetic field. In this way, an electric current is induced in the conductor 15 as a function of a varying magnetic field B generated by the magnetic field generator element 1, wherein at least one parameter of the varying magnetic field B is controlled by the control element 12.

Based on the preferential execution previously stated, in which the conductor 15 is a metallic knee prosthesis made of chromium cobalt, the magnetic field generator element 11 is a toroidal coil, and the support element 14 is a knee brace, the magnetic field generator element 11 is held internally to the support element 14. Furthermore, when the control element 12 is electrically assembled to the magnetic field generator element 11, the control element 12 is also held inside the support element 14. Thus, both elements, the control element 12 and the magnetic field generator 11, are held inside the support element 14.

However, and as mentioned above, such execution should not be understood as a limitation of this invention, being only one example of the possible executions. Alternatively, the magnetic field generator element 11 and the control element 12 can be arranged outside of the support element 14, so that the support element 14 is configured to serve, for example, as a holder.

Moreover, since the magnetic field generator element 11 may be any known element of the state of the art able to generate a varying magnetic field, the support element 14 should not have its dimensions specifically linked to the dimensions of the magnetic field generator element 11.

That is, the support element 14 can be a knee brace, as defined in the preferential execution of this invention, as well as can be a metal holder, a box, a casing, a cover, coating, etc., i.e. any apparatus fit to support the magnetic field generator element 11.

Similarly, the magnetic field generator element 11 is only preferably a toroidal coil, but such an execution should not be understood as a limitation of the present invention, as it was already mentioned earlier.

Anyway, when it is operating, the control element 12 controls at least one varying parameter of the varying magnetic field B generated by the magnetic field generator element 11. Thus, it is possible to control, as a function of the control of this varying parameter, the values of the electric current induced on the conductor 15 such as, for example, the intensity i of the current, its polarity, frequency, modulation, etc. That is, the control element 12 is also designed to control the values of the parameters of the induced electrical current on the conductor 15.

In particular, the control element 12 is also designed to control the period of time in which the magnetic field will be generated by the magnetic field generator element 11 and, therefore, the period of time in which the electric current will be induced in conductor 15.

Regarding the intensity i of the electrical current induced in conductor 15, preferably only, the electric current has an intensity i that is in the range between 0.2 mA to 2 mA. However, such a range should not be understood as a limitation of the present invention, being only a preferential range established in relation to the preferential execution described here. That is, the induced electric current in the conductor 15 may have any desired value depending on the desired results in the period of time in which the device 10 will be operated.

Furthermore, and in harmony with the information described above, the present invention refers to a method to generate an electric current in a conductor 15, by means of a device 10 capable of generating the electric current in that conductor 15.

This method comprises the following steps:
(a) to establish at least one value for at least one parameter of the desired electric current;
(b) to establish a period of time of operating the device 10;
(c) to adjust at least one variable parameter;
(d) to generate a variable magnetic field B;
(e) to approach the device 10 to the conductor 15; and
(f) to induce an electric current on the conductor 15.

Moreover, this method represents only a preferred operation of the device 10, in which the steps (a) and (b) are performed by the user. That is, the desired current and time period values that the current will be induced in conductor 15 are defined by the user, prior to the operation of the device 10.

In this way, once defined the values of at least one parameter of the current and the period of time, the varying parameter of the magnetic field can be adjusted through the control element 12 so that an electric current with the characteristics above defined is induced on the conductor 15.

Moreover, in the only preferential execution described above, the device 10 is located inside the support element 14, so that the electric current is induced in the conductor 15 when the device 10 approaches the conductor 15.

In other words, and only in reference to the preferential execution described here, an electrical current will be induced when the device 10 inside the knee brace approaches the knee prosthesis when the user wears the knee brace.

Moreover, and in harmony with the information presented earlier, the present invention relates to a method of removing biofilm from a conductor 15 inside the body of a patient using a device 10 capable to generate an electric current with at least one varying parameter on that conductor 15.

This method to remove the biofilm from a conductor 15 inside the body of a patient comprises the following steps:
(i) to establish at least one varying parameter of the electrical current required for the treatment of the biofilm on the conductor 15,
(ii) to establish the period of time in which the electric current will be applied to the conductor 15,
(iii) to position the support element 14 in the region of the body of the patient where the conductor 15 is located,
(iv) to activate the device 10, and
(v) to generate an electrical current with an intensity i established in step i, during the period of time established in step ii.

Thus, and as mentioned earlier, the activation of device 10 will result in the generation of a B magnetic field with at least one varying parameter that, in turn, will induce an electric current with at least one varying parameter in the conductor 15. Such induction of the electric current is, in an advantageous way, responsible for the removal and/or treatment of the biofilm present in the conductor 15.

Moreover, and in an only preferential way, in a possible execution of the present method, the varying parameter of the electric current is at least one of the following: the intensity i of the electric current, the polarity of the electric current, the frequency of the electric current, and the modulation of the electric current.

In addition, in this only preferred execution, the conductor 15 is a metallic implant, and more preferably still, it is a metallic prosthesis.

Furthermore, the present invention refers to a method of treatment of a subject requiring removal of the biofilm on a metallic prosthesis 15 implanted inside his body. The method comprises the following steps:
(a) to establish one value for at least one parameter of the desired electric current;
(b) to establish a period of time for operating the device (10);
(c) to adjust at least one varying parameter of the varying magnetic field B;
(d) to generate a varying magnetic field B;
(e) to approach the device 10 to the metallic implant 15; and
(f) to induce an electric current on the metallic implant 15

Since an example of execution has been described, it should be understood that the scope of this invention covers other possible variations, being limited only by the content of the aforementioned claims, including the possible equivalents.

The invention claimed is:

1. A portable device able to generate, in a noninvasive manner, an electric current in an implant during a period of time, wherein the generated electric current comprises at least one parameter and is configured to remove and/or prevent the formation of a biofilm in said implant,
wherein the device comprises a toroidal magnetic field generator element, a control element, a support element, and an energy source,
the toroidal magnetic field generator element, the control element, and the energy source are electrically assembled to each other, the energy source being configured to electrically feed the elements of the portable device,
the toroidal magnetic field generator element is configured to generate a varying magnetic field comprising at least one varying parameter, said varying magnetic field being configured to generate said electric current,
the control element is configured to control the at least one varying parameter of the varying magnetic field, wherein said at least one varying parameter is at least one physical variable of the varying magnetic field, and
the support element is configured to hold the energy source, the magnetic field generator element, and the control element,
wherein the support element is at least one of the following: a knee brace or an elbow brace,
the at least one parameter of the generated electric current is related to at least one of the following: intensity of the electric current, polarity of the electric current, frequency of the electric current, and modulation of the electric current.

2. The device able to generate an electric current in a conductor, according to claim 1, wherein the implant is a knee prosthesis and is made of at least one of the following: titanium, steel, Teflon, chrome-cobalt.

3. The device able to generate an electric current in a conductor, according to claim 1, wherein the control element is a microprocessor.

4. The device able to generate an electric current in a conductor, according to claim 1, wherein the at least one varying parameter of the varying magnetic field is at least one of the following: an intensity of the varying magnetic field, a polarity of the varying magnetic field, a frequency of the varying magnetic field, and a position of the varying magnetic field.

5. The device able to generate an electric current in a conductor, according to claim 1, wherein the energy source is a battery.

* * * * *

UNITED STATES PATENT AND TRADEMARK OFFICE
CERTIFICATE OF CORRECTION

| | |
|---|---|
| PATENT NO. | : 11,986,393 B2 |
| APPLICATION NO. | : 16/748330 |
| DATED | : May 21, 2024 |
| INVENTOR(S) | : Pacca |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 893 days.

Signed and Sealed this
Twentieth Day of May, 2025

Coke Morgan Stewart
*Acting Director of the United States Patent and Trademark Office*